United States Patent [19]

Wright, Jr. et al.

[11] Patent Number: 4,619,941

[45] Date of Patent: Oct. 28, 1986

[54] N-[(1H-IMIDAZOL-1-YL)ALKYL]-1H-INDOLECARBOXAMIDES USEFUL AS THROMBOXANE SYNTHETASE INHIBITORS AND ANTIHYPERTENSIVE AGENTS

[75] Inventors: William B. Wright, Jr., Woodcliff Lake; Jeffery B. Press, Rocky Hill, both of N.J.

[73] Assignee: American Cyanamid Company, Stamford, Conn.

[21] Appl. No.: 673,066

[22] Filed: Nov. 19, 1984

[51] Int. Cl.[4] .................. A61K 31/415; C07D 403/12
[52] U.S. Cl. ..................................... 514/397; 548/336
[58] Field of Search ......................... 548/336; 514/397

[56] References Cited

U.S. PATENT DOCUMENTS 4,489,089  12/1984  Wright et al. ..................... 548/336

Primary Examiner—Richard A. Schwartz
Assistant Examiner—Kurt G. Briscoe
Attorney, Agent, or Firm—Gregg C. Benson

[57] ABSTRACT

This invention discloses novel N-[(1H-imidazol-1-yl)alkyl]-1H-indolecarboxamides which are useful as inhibitors of thromboxane synthetase and/or as antihypertensive agents in the treatment of hypertension and myocardial ischemia.

36 Claims, No Drawings

N-[(1H-IMIDAZOL-1-YL)ALKYL]-1H-INDOLECARBOXAMIDES USEFUL AS THROMBOXANE SYNTHETASE INHIBITORS AND ANTIHYPERTENSIVE AGENTS

SUMMARY OF THE INVENTION

This invention relates to new organic compounds and, more particularly, is concerned with novel N-[(1H-imidazol-1-yl)alkyl]-1H-indolecarboxamides which may be represented by the following structural formula:

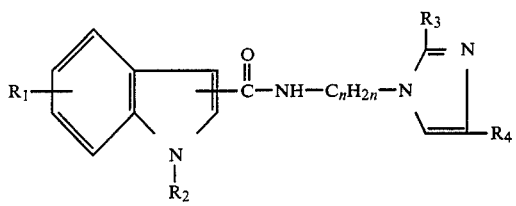

wherein $R_1$ is selected from the group consisting of hydrogen, halogen, lower alkyl($C_1$-$C_3$) and alkoxy ($C_1$-$C_3$); $R_2$ is selected from the group consisting of hydrogen, lower alkyl ($C_1$-$C_3$) and benzyl; n is an integer from 2 to 8; $R_3$ and $R_4$ may be the same or different and are selected from the group consisting of hydrogen, lower alkyl($C_1$-$C_3$) and phenyl; together with the pharmaceutically acceptable salts thereof.

The novel compounds of the present invention are obtainable, in general, as white or pale yellow crystalline solids having characteristic melting points and absorption spectra. They are appreciably soluble in many organic solvents such as lower alkanols, chloroform, dichloromethane, chlormethane, tetrahydrofuran, acetone, N,N-dimethylformamide and the like, but are relatively insoluble in water.

The organic bases of this invention form non-toxic acid-addition salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic sulfamic, citric, lactic, malic, succinic, maleic, fumaric, tartaric, acetic, benzoic, gluconic, ascorbic and the like. For purposes of this invention the free bases are equivalent to their nontoxic acid-addition salts. The acid-addition salts of the organic bases of this invention are relatively soluble in water, methanol and ethanol but relatively insoluble in nonpoplar organic solvents such as diethyl ether, benzene and toluene.

This invention also pertains to N-[(1H-imidazol-1-yl)alkyl]-1H-isoindole-1,3(2H)-diones which may be represented by the following structural formula:

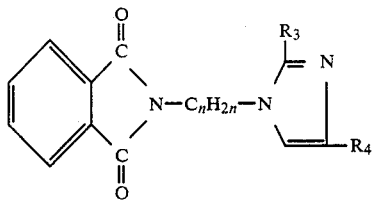

wherein n is an integer from two to eight, inclusive and $R_3$ and $R_4$ are as hereinbefore defined. These phthalamide derivatives are intermediates for the preparation of 1H-imidazole-1-alkanamines useful in the preparation of the novel N-[(1H-imidazol-1-yl)alkyl]-1H-indolecarboxamides hereinabove described.

DETAILED DESCRIPTION OF THE INVENTON

The compounds of the present invention may be prepared according to the following reaction schemes wherein $R_1$, $R_2$, $R_3$, $R_4$ and n are as described hereinabove.

METHOD I

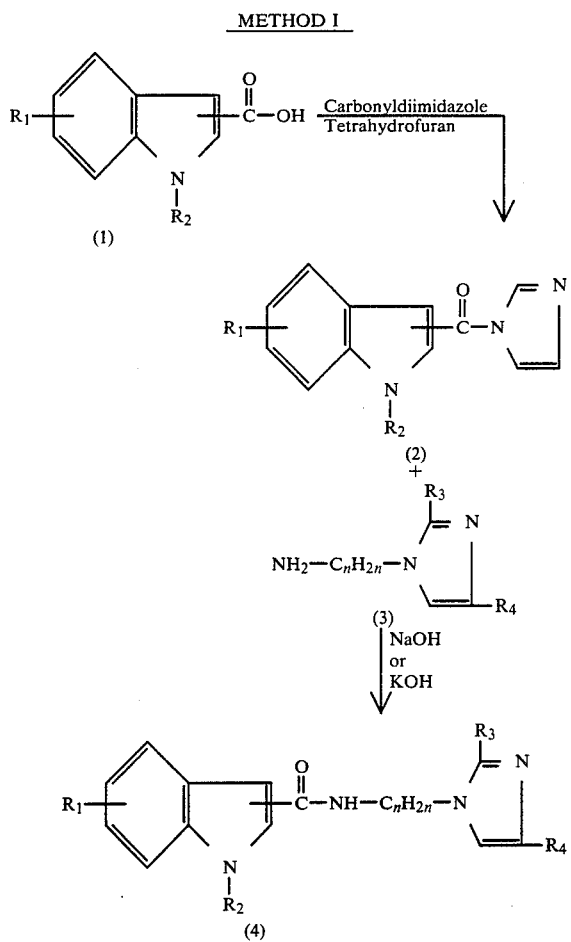

In accordance with Method I, an appropriately substituted indole carboxylic acid (1) is reacted with 1,1'-carbonyldiimidazole in an inert solvent such as dioxane or tetrahydrofuran at ambient temperatures for 1–3 hours to provide the intermediates (2). Treatment of the intermediates (2) with an appropriately substituted 1H-imidazole-1-alkanamine (3), either as the free base or a salt thereof, provides the final products (4). The final condensation of (2) and (3) is best carried out by merely adding (3) to the reaction mixture and allowing it to stand at room temperature or, preferably, heating at reflux for about 2–6 hours. Addition of aqueous base (potassium hydroxide or sodium hydroxide) and a solvent such as chloroform or carbon tetrachloride results in isolation of the product (4) from the organic phase.

The 1,3(2H)-dione intermediates (7) of the present invention may be readily prepared and used to prepare the 1H-imidazole-1-alkanamines (3) as set forth in the following reaction scheme (Method II) wherein n, $R_3$ and $R_4$ are as hereinbefore defined and X is chloro or bromo.

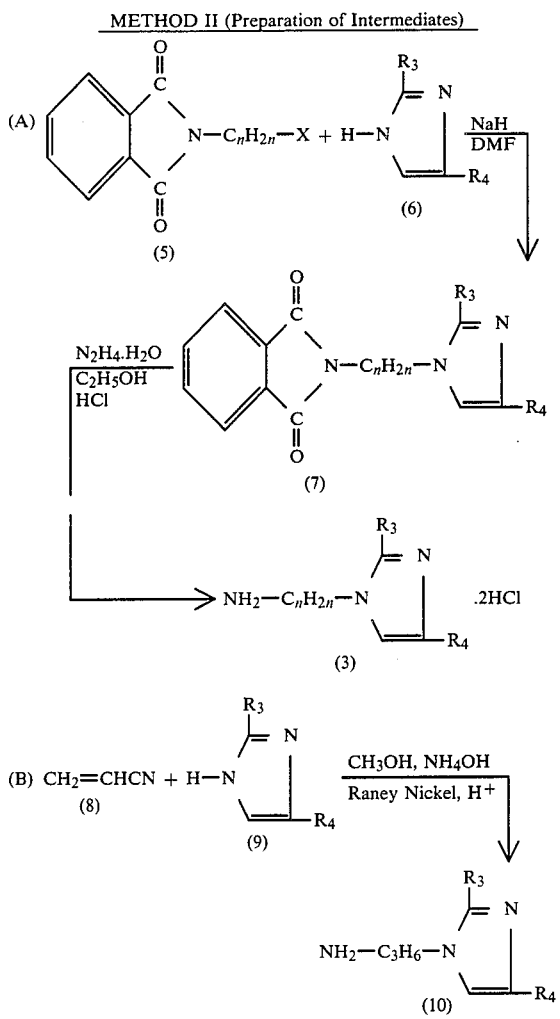

METHOD II (Preparation of Intermediates)

In accordance with Method IIA, an appropriately substituted imidazole (6) is first converted to a salt form with sodium amide, sodium hydride, and the like and then condensed with an appropriate N-haloalkylphthalimide (5) for about 4–8 hours, to obtain the 1,3(2H)-dione intermediate (7), which is then reacted with hydrazine hydrate in ethanol at reflux for about 2–8 hours. Hydrochloric acid is then added and refluxing is continued for about 1–6 hours, giving the 1H-imidazole-1-alkanamine, dihydrochloride (3). The dihydrochloride (3) may be converted to the free base by treatment of an aqueous solution of the dihydrochloride with sodium hydroxide or potassium hydroxide and extraction into a solvent such as chloroform or dichloromethane, then isolation from the organic phase.

In accordance with Method IIB, acrylonitrile (8) and an imidazole (9) are reacted with heat for about 2–4 hours, concentrated to an oil and then hydrogenated with Raney nickel catalyst in methanol and ammonium hydroxide for a period of about 8–10 hours, giving 1H-imidazole-1-propanamine derivatives (10).

The compounds of this invention inhibit thromboxane synthetase enzyme without interfering with other enzymes in the arachadonic acid cascade. Thus, these compounds are useful in the treatment of diseases characterized by an imbalance of thromboxane $A_2$/prostacyclin such as ischemic heart disease, transient ischemic attack, thrombosis and migraine. Recent reviews have established the role of the thromboxane/prostacyclin balance in the vascular system [Cardiovascular Diseases: New Trends in Surgical and Medical Apsects, H. Barnett, P. Paoletti, E. Flamm and G. Brambilla, eds., Elsevier/North-Holland Biomedical Press, pp 137–150 (1981)]. Prostacyclin ($PGI_2$) is a potent vasodilator and platelet aggregation inhibitor, whereas thromboxane ($TXA_2$) is a powerful vasoconstrictor and causative of platelet aggregation. $TXA_2$ is synthesized by thromboxane synthetase enzyme located in, for example, blood platelets. When $TXA_2$ production is increased relative to $PGI_2$, platelet aggregation, thrombosis and vasospasm may occur [Lancet, 1, 1216 (1977); Lancet, 1, 479 (1977); Science, 193, 1135 (1976); Amer. J. Cardiology, 41, 787 (1978)]. $TXA_2$ synthetase inhibitors have been shown to have superior anti-thrombotic action to that of aspirin [J. Clin. Invest., 65, 400 (1980); Br. J. Pharmac., 76, 3 (1982)].

The role of prostaglandins including $TXA_2$ and $PGI_2$ in ischemic heart patients has been reviewed [Cardiovascular Pharmacology of the Prostaglandins, A. G. Herman, P. M. Vanhoute, H. Denolin and A. Goosens, eds., Raven Press, New York, pp 361–374 (1982)]. Injection of $TXA_2$ into coronary arteries of guinea pigs and rabbits causes myocardial ischemia and subendocardial necrosis [Drugs of the Future, 7, 331 (1982); Proc. Jap. Acad., 53(B), 38 (1977); Eur. J. Pharmacol., 53 49(1978)]. Recent research has demonstrated the beneficial effects of $PGI_2$ and selective inhibition of thromboxane synthetase on ischemic myocardium in canines [J. Cardiovascular Pharmacology, 4, 129 (1982)]. Thus compounds which selectively inhibit thromboxane synthetase (and hence $TXA_2$) without adversely affecting $PGI_2$ are useful in the treatment of vascular diseases such as ischemia and migraine. In addition, inhibition of $TXA_2$ formation may effectively treat platelet aggregation and prevent thrombosis.

The inhibition of thromboxane ($TXA_2$) formation was studied by determining the concentration of thromboxane $B_2$ ($TXB_2$), the stable hydrolysis product of $TXA_2$.

Under urethan anesthesia, 10 μl of arterial blood was collected in one ml of 3.2% sodium citrate in a polystyrene tube from Okamoto-Aoki spontaneously hypertensive rats (SHR) (Taconic Farms, Germantown, N.Y.) between 19 and 24 weeks in age. The blood was diluted with 3 ml cold saline and centrifuged at room temperature for 15 minutes at 460 xg. The platelet rich plasma (PRP) was separated. The platelets were isolated by centrifuging the PRP for 10 minutes at 1060 xg and were washed in 4 ml cold oxygenated Krebs phosphate buffer, pH 7.4. the chilled platelets recovered from centrifuging at 800 xg for 10 minutes were resuspended in oxygenated Krebs phosphate buffer and diluted to contain $4.5–6.0 \times 10^4$ platelets/μl. Assay samples, prepared on ice, contained 200 μl platelet suspension, 50 μl saline, and 50 μl vehicle or drug under study (OKY-1581, UK-37248-01, 1-benzylimidazole, or indomethacin). The samples were incubated for 10 minutes at 37° C. in a metabolic shaker. The reaction was terminated by immersing the tubes in an ice bath and adding 50 μl of 0.5 M citric acid. The samples were centrifuged for 10 minutes in a refrigerated centrifuge and the supernatants thus obtained were decanted and stored at −20° C. The $TXB_2$ content for each sample was determined by a direct radioimmunoassay (RIA) utilizing a TXB$_2$ specific RIA kit purchased from New England Nuclear, Boston, MA and expressed as pg TXB$_2$ formed minute$^{-1}$ sample$^{-1}$, from which the percent inhibition of TXB$_2$ formation was calculated. The results of this test on representative compounds of this invention appear in Table I below.

TABLE I

| Compound | Dose (M) | % Inhibition |
|---|---|---|
| N—[3-(1H—Imidazol-1-yl)propyl]-1-methyl-1H—indole-2-carboxamide | 10$^{-4}$ | 88 |
| N—[3-(1H—Imidazol-1-yl)propyl]-5-methoxy-1H—indole-2-carboxamide | 10$^{-4}$ | 96 |
| N—[3-(1H—Imidazol-1-yl)propyl]-1H—indole-2-carboxamide | 10$^{-4}$ | 94 |
| 5-Chloro-N—[3-(1H—imidazol-1-yl)propyl]-1H—indole-2-carboxamide | 10$^{-4}$ | 95 |
| 5-Chloro-N—[8-(1H imidazol-1-yl)octyl]-1H—indole-2-carboxamide | 10$^{-4}$ | 66 |
| 5-Chloro-N—[3-(1H—imidazol-1-yl)butyl]-1H—indole-2-carboxamide | 10$^{-4}$ | 98 |
| 5-Chloro-N—[3-(1H—imidazol-1-yl)-2-methylpropyl]-1H—indole-2-carboxamide | 10$^{-4}$ | 100 |
| 1-Methyl-N—[3-(4-methyl-1H—imidazol-1-yl)propyl]-1H—indole-2-carboxamide | 10$^{-4}$ | 85 |
| N—[3-(4-Methyl-1H—imidazol-1-yl)propyl]-1H—indole-2-carboxamide | 10$^{-4}$ | 100 |
| 5-Chloro-N—[3-(4-methyl-1H—imidazol-1-yl)propyl]-1H—indole-2-carboxamide | 10$^{-4}$ | 100 |
| N—[4-(1H—Imidazol-1-yl)butyl]-1H—indole-2-carboxamide | 10$^{-4}$ | 100 |
| 5-Methoxy-N—[4-(1H—imidazol-1-yl)butyl]-1H—indole-2-carboxamide | 10$^{-4}$ | 100 |
| N—[3-(2-Methyl-1H—imidazol-1-yl)propyl]-1H—indole-2-carboxamide | 10$^{-4}$ | 44 |
| 5-Methoxy-N—[3-(2-methyl)-1H—imidazol-1-yl)propyl]-1H—indole-2-carboxamide | 10$^{-4}$ | 49 |
| N—[3-(2-Phenyl-1H—imidazol-1-yl)propyl]-1H—indole-2-carboxamide | 10$^{-4}$ | 91 |
| 1-Methyl-N—[3-(2-methyl-1H—imidazol-1-yl)propyl]-1H—indole-2-carboxamide | 10$^{-4}$ | 56 |

The novel compounds of the present invention also are active antihypertensive agents and were tested for hypotensive activity by the method of P. S. Chan and D. Poorvin, *Clinical and Experimental Hypertension*, 1 (6), 817–830 (1979). Male, 16 week old, spontaneously hypertensive rats of the Okamoto strain, from Taconic Farms, Germantown, N.Y., having an average means arterial blood pressure of 160±1.5 mm of mercury are used in the test. One to three rats are used per test compound. A rat is dosed by gavage with a test compound, suspended in 2% pre-boiled starch at a concentration of 50 mg/ml, at a dose of 100 mg/kg of body weight or less with 0.9% sodium chloride loading at a dose of 25 ml/kg of body weight. A second identical dose of the test compound, without sodium chloride loading is given 24 hours later. At 28 hours after the initial dose the mean arterial blood pressure is measured by the method of Chan and Poorvin vide supra. The procedure is repeated in a second and third rat when necessary.

The results of this test on representative compounds of the present invention appear in Table II below.

TABLE II

| Compound | MABP in mm Hg (no. of rats) |
|---|---|
| N—[3-(1H—Imidazol-1-yl)propyl]-1H—indole-2-carboxamide | 114 (2) |
| N—[3-(1H—Imidazol-1-yl)propyl]-1H—indole-5-carboxamide | 133 (3) |
| 1-Methyl-N—[3-(4-methyl-1H—imidazol-1-yl)propyl]-1H—indole-2-carboxamide | 136 (2) |
| N—[3-(4-Methyl-1H—imidazol-1-yl)propyl]-1H—indole-2-carboxamide | 131 (4) |
| 5-Chloro-N—[3-(4-methyl-1H—imidazol-1-yl)propyl]-1H—indole-2-carboxamide | 135 (2) |
| N—[4-(1H—Imidazol-1-yl)butyl]-1H—indole-2-carboxamide | 137 (3) |
| 5-Chloro-N—[3-(1H—imidazol-1-yl)butyl]-1H—indole-2-carbonxamide | 119 (2) |
| 5-Chloro-N—[3-(1H—imidazol-1-yl)-2-methylpropyl]-1H indole-2-carboxamide | 123 (3) |
| 5-Methoxy-N—[4-(1H—imidazol-1-yl)butyl]-1H—indole-2-carboxamide | 130 (3) |
| 5-Chloro-N—[5-(1H—imidazol-1-yl)pentyl]-1H—indole-2-carboxamide | 124 (4) |
| 5-Chloro-N—[4-(1H—imidazol-1-yl)butyl]-1H—indole-2-carboxamide | 118 (3) |

The novel compounds of the present invention have been found to be highly useful for inhibiting thromboxane synthetase and/or lowering elevated blood pressure in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units are employed that a total of from about 35 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weight of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-alpha-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention and should not be construed to limit this invention in any way.

EXAMPLE 1

1H-imidazole-1-propanamine

A mixture of 41 g of imidazole and 75 ml of acrylonitrile was heated on a steam bath for 3 hours, then concentrated under reduced pressure to remove excess acrylonitrile. A 300 ml portion of methanol was added to the residue together with 100 ml of concentrated ammonium hydroxide and 8 g of Raney nickel catalyst. This mixture was hydrogenated in a Parr apparatus until hydrogen uptake ceased and then filtered giving a light green liquid. A 300 ml portion of tetrahydrofuran was added to this liquid and the mixture filtered through diatomaceous earth. The filtrate was concentrated twice from toluene, giving 75.2 g of the desired intermediate as a clear oil. The dihydrochloride salt may be obtained by treating the base with ethanolic hydrochloric acid, concentration and recrystallization from ethanol.

By substituting crotonitrile or methacrylonitrile for acrylonitrile in the above procedure, 3-(1H-imidazole)-1-butanamine or 3-(1H-imidazole)-2-methyl-1-propanamine, is obtained respectively.

EXAMPLE 2

4-Methyl-1H-imidazole-1-propanamine

A mixture of 49.2 g of 4-methyl-1H-imidazole and 75 ml of acrylonitrile was heated on a steam bath for 6 hours and then concentrated to remove excess acrylonitrile. The residue was diluted with 400 ml of methanol and divided into two parts. To each was added 90 ml of ammonium hydroxide and Raney nickel catalyst. Each portion was then hydrogenated in a Parr apparatus. Each part was filtered, the filtrates combined and concentrated. The residue was concentrated from toluene. This residue was dissolved in tetrahydrofuran, stirred for one hour, filtered, concentrated, then concentrated from toluene, giving 82.2 g of the desired intermediate as an oil. Alternatively, and preferably, the portions can be purified by distillation through a Kugelrohr apparatus to produce the desired intermediate as an oil.

By substituting the appropriate imidazole starting material in the above procedure, the following intermediates were prepared: 2-methyl-1H-imidazole-1-propanamine; 2-ethyl-1H-imidazole-1-propanamine; 2,4-dimethyl-1H-imidazole-1-propanamine; 2-phenyl-1H-imidazole-1-propanamine; and 4-phenyl-1H-imidazole-1-propanamine.

EXAMPLE 3

1H-Imidazole-1-butanamine

A mixture of 0.2 mole of 2-[4-(1H-imidazol-1-yl)butyl]-1H-isoindole-1,3(2H)-dione, 0.22 mole of hydrazine hydrate and 400 ml of ethanol was heated on a steam bath for 3 hours and then treated with 400 ml of 3N hydrochloric acid and heated at reflux for an additional 2 hours. The insoluble material was filtered off and the mother liquor was concentrated to a low volume and again filtered. The remainder of the volatile material was distilled off and the residue was treated with saturated potassium carbonate solution. The 1H-imidazole-1-butanamine was extracted into methylene chloride and further purified by distillation on a Kugelrohr apparatus. In like manner from the appropriate 2-[ω-(1H-imidazol-1-yl)alkyl]-1H-isoindole-1,3(2H)-dione were prepared 1H-imidazole-1-pentanamine; 1H-imidazole-1-hexanamine; 1H-imidazole-1-heptanamine; and 1H-imidazole-1-octanamine.

EXAMPLE 4

2-[4-(1H-Imidazol-1-yl)butyl]-1H-isoindole-1,3(2H)-dione

A mixture of 0.2 mole of N-(4-bromobutyl)-1H-isoindole-1,3(2H)-dione, 0.22 mole of sodium imidazole and 300 ml of dimethylformamide was stirred at 100° C. for 8 hours and then concentrated to remove the dimethylformamide. The residue was boiled with 500 ml of toluene and the insoluble material was removed by filtration. The toluene layer was concentrated to remove the solvent and the residue was further purified by HPLC using ethyl acetate and a silica gel column. The desired compound melted at 75°–77° C. Addition of ethanolic hydrogen chloride resulted in the hydrochloride salt, mp 200°–203° C.

When the above procedure was used to react sodium imidazole with the appropriate 2-(ω-bromoalkyl)-1H-isoindole-1,3(2H)-dione, the compounds of Table III were obtained.

TABLE III

| Ex. | Compound | MP °C. |
|---|---|---|
| 5 | 2-[5-(1H—imidazol-1-yl)pentyl]-1H—isoindole-1,3(2H)—dione hydrochloride | 194–197 |
| 6 | 2-[6-(1H—imidazol-1-yl)hexyl]-1H—isoindole-1,3(2H)—dione | 83–87 |
| 7 | 2-[7-(1H—imidazol-1-yl)heptyl]-1H—isoindole-1,3(2H)—dione | oil |
| 8 | 2-[8-(1H—imidazol-1-yl)octyl]-1H—isoindole-1,3(2H)—dione | 43–45 |

EXAMPLE 9

N-[3-(1H-Imidazol-1-yl)propyl]-1-methyl-1H-indole-2-carboxamide

A mixture of 1.75 g of 1-methylindole-2-carboxylic acid and 1.62 g of 1,1′-carbonyldiimidazole in 30.0 ml of tetrahydrofuran was stirred at room temperature for 2 hours. A 1.98 g amount of 1H-imidazole-1-propanamine dihydrochloride was added and the mixture was stirred for 16 hours. The mixture was heated at reflux for 2 hours, treated with 10 ml of water and heated one hour longer, then concentrated to remove solvent. A 25 ml portion of 1N sodium hydroxide was added to the residue followed by dichloromethane. The mixture was swirled, mixed, evaporated, washed twice with water, dried and concentrated and gave 2.1 g of an oil. The oil was triturated with ether and gave 0.55 g of the desired compound as white crystals, mp 125°–129° C.

Following the general procedure of Example 9 and reacting the appropriate carboxylic acid derivative with 1,1′-carbonyldiimidazole and 1H-imidazol-1-propanamine in tetrahydrofuran, the products of Examples 10–15 found in Table IV were prepared.

TABLE IV

| Ex. | Carboxylic Acid | Compound | MP °C. |
|---|---|---|---|
| 10 | 5-Methoxy-indole-2-carboxylic acid | N—[3-(1H—Imidazol-1-yl)-propyl]-5-methoxy-1H—indole-2-carboxamide | 204–207 |
| 11 | Indole-2-carboxylic acid | N—[3-(1H—Imidazol-1-yl)-propyl]-1H—indole-2-carboxamide | 197–199 |
| 12 | Indole-5-carboxylic acid | N—[3-(1H—Imidazol-1-yl)-propyl]-1H—indole-5-carboxamide | 179–181 |
| 13 | 5-Chloroindole-2-carboxylic acid | 5-Chloro-N—[3-(1H—imidazol-1-yl)propyl]-1H—indole-2-carboxamide | 223–225 |
| 14 | 5-Methylindole-2-carboxylic acid | N—[3-(1H—Imidazol-1-yl)-propyl]-5-methyl-1H—indole-2-carboxamide | oil |
| 15 | 5-Fluoroindole-2-carboxylic acid | 5-Fluoro-N—[3-(1H—imidazol-1-yl)propyl]-1H—indole-2-carboxamide | 225–227 |

EXAMPLE 16

1-Methyl-N-[3-(4-methyl-1H-imidazol-1-yl)propyl]-1H-indole-2-carboxamide

A mixture of 5.26 g of 1-methylindole-2-carboxylic acid and 4.86 g of 1,1′-carbonyldiimidazole in 100 ml of tetrahydrofuran was stirred at room temperature for 3 hours. Then 4.6 g of 4-methyl-1H-imidazole-1-propanamine was added and stirring was continued for 16 hours. The mixture was heated at reflux for 3 hours, 15 ml of water was added and refluxing was continued for 2 hours longer. The mixture was concentrated, then 200 ml of dichloromethane and 30 ml of 1N sodium hydroxide were added. The mixture was shaken and the dichloromethane layer was separated and washed twice with water, dried over magnesium sulfate, filtered and evaporated to an oil. The oil was triturated with ether and gave pale yellow crystals. Recrystallization from ethyl acetate gave 6.02 g of the compound of the Example as pale yellow crystals, mp 137°–142° C.

Following the general procedure of Example 16 and reacting the appropriate carboxylic acid derivative with 4-methyl-1H-imidazole-1-propanamine and 1,1′-carbonyldiimidazole in tetrahydrofuran, the compounds of Examples 17–18 found in Table V were prepared.

TABLE V

| Ex. | Carboxylic Acid | Compound | MP °C. |
|---|---|---|---|
| 17 | Indole-2-carboxylic acid | N—[3-(4-Methyl)-1H—imidazol-1-yl)propyl]-1H—indole-2-carboxamide | 209–213 |
| 18 | 5-Chloroindole-2-carboxylic acid | 5-Chloro-N—[3-(4-methyl-1-H—imidazol-1-yl)propyl]-1H—indole-2-carboxamide | 232–235 |

EXAMPLE 19

If 2-ethyl-1H-imidazole-1-propanamine is substituted for 4-methyl-1H-imidazole-1-propanamine in the procedure of Example 16, N-[3-(2-ethyl-1H-imidazol-1-yl)propyl]-1-methyl-1H-indole-2-carboxamide is obtained.

EXAMPLE 20

N-[4-(1H-Imidazol-1-yl)butyl]-1H-indole-2-carboxamide

A mixture of 1.61 g of indole-2-carboxylic acid and 1.62 g of 1,1′-carbonyldiimidazole in 30 ml of tetrahydrofuran was stirred at room temperature for 3 hours, then 1.39 g of 1H-imidazole-1-butanamine was added and stirring was continued for 16 hours. The mixture was heated at reflux for 2 hours then 10 ml of water was added and heating was continued for one hour longer. The mixture was concentrated and then about 70 ml of dichloromethane and 10 ml of 1N sodium hydroxide were added with shaking. The organic layer was separated, washed twice with water, dried over magnesium sulfate, filtered and evaporated to an oil. Trituration with either gave 2.1 g of the desired compound as yellow crystals.

Following the general procedure of Example 20 and reacting the appropriate carboxylic acid derivative with 1,1′-carbonyldiimidazole and 1H-imidazole-1-butanamine in tetrahydrofuran, the compounds of Examples 21 and 22 found in Table VI were prepared and the compound of Example 23 in Table VI is prepared.

TABLE VI

| Ex. | Carboxylic Acid | Compound | MP °C. |
|---|---|---|---|
| 21 | 5-Methoxy-indole-2-carboxylic acid | 5-Methoxy-N—[4-(1H—imidazol-1-yl)butyl]-1H—indole-2-carboxamide | 185–187 |
| 22 | 5-Chloro-indole-2-carboxylic acid | 5-Chloro-N—[4-(1H—imidazol-1-yl)butyl]-1H—indole-2-carboxamide | 183–185 |
| 23 | 1-Benzyl-indole-2-carboxylic acid | 1-Benzyl-N—[4-(1H—imidazol-1-yl)butyl]-1H—indole-2-carboxamide | |

EXAMPLE 24

N-[3-(2-Methyl-1H-imidazol-1-yl)propyl]-1H-indole2-carboxamide

A mixture of 3.23 g of indole-2-carboxylic acid and 3.24 g of 1,1'-carbonyldiimidazole in 60 ml of tetrahydrofuran was stirred at room temperature for 2 hours. Then 2.78 g of 2-methyl-1H-imidazolepropanamine was added and stirring was continued for 16 hours. The mixture was then heated at reflux for 2 hours, 15 ml of water was added and heating was continued for one hour longer. The mixture was concentrated and about 70 ml of dichloromethane was added plus 10 ml of 1N sodium hydroxide with swirling. The precipitate which formed was collected by filtration, washed with water and gave 4.8 g of the desired compound as white crystals, mp 235°–237° C.

Following the general procedure of Example 24 and reacting the appropriate carboxylic acid derivative with 1,1'-carbonyldiimidazole and 2-methyl-1H-imidazolepropanamine in tetrahydrofuran the compounds of Examples 25–27 found in Table VII were prepared, and the compound of Example 28 in Table VII is prepared.

TABLE VII

| Ex. | Carboxylic Acid | Compound | MP °C. |
|---|---|---|---|
| 25 | 5-Methoxy-indole-2-carboxylic acid | 5-Methoxy-N—[3-(2-methyl-1H—imidazol-1-yl)-propyl]-1H—indole-2-carboxamide | 235–237 |
| 26 | Indole-5-carboxylic acid | N—[3-(2-Methyl-1H—imidazol-1-yl)propyl]-1H—indole-5-carboxamide | 212–214 |
| 27 | 1-Methylindole-2-carboxylic acid | 1-Methyl-N—[3-(2-methyl-1H—imidazol-1-yl)-propyl]-1H—indole-2-carboxamide | 190–192 |
| 28 | 5-Bromoindole-2-carboxylic acid | 5-Bromo-1-methyl-N—[3-(2-methyl-1H—imidazol-1-yl)propyl]-1H—indole-2-carboxamide | |

EXAMPLE 29

5-Chloro-N-[5-(1H-imidazol-1-yl)pentyl]-1H-indole-2-carboxamide

A mixture of 0.90 g of 5-chloroindole-2-carboxylic acid and 0.74 g of 1,1'-carbonyldiimidazole in 25 ml of tetrahydrofuran was stirred at room temperature for 3 hours. Then 0.70 g of 1H-imidazole-1-pentanamine in 25 ml of tetrahydrofuran was added and stirring was continued for 16 hours. The mixture was heated at reflux for 5 hours, 5 ml of water was added and heating was continued for one hour longer. The mixture was concentrated, then one ml of 5N sodium hydroxide and about 25 ml of dichloromethane was added with shaking. The organic layer was separated and filtered and gave 1.2 g of the compound of the Example as white crystals, mp 214°–216° C.

EXAMPLE 30

5-Chloro-N-[6-(1H-imidazol-1-yl)hexyl]-1H-indole2-carboxamide

When 5-chloroindole-2-carboxylic acid is reacted with 1,1'-carbonyldiimidazole and 1H-imidazole-1-hexanamine by the procedure of Example 29, the compound of the Example is obtained.

EXAMPLE 31

5-Chloro-N-[8-(1H-imidazol-1-yl)octyl]-1H-indole-2-carboxamide

When 1H-imidazole-1-octanamine was substituted for 1H-imidazole-1-pentanamine in the procedure of Example 29, the compound of the example, mp 187°–189° C., was obtained.

EXAMPLE 32

5-Chloro-N-[2-(1H-imidazol-1-yl)ethyl]-1H-indole-2-carboxamide

A mixture of 1.8 g of 5-chloroindole-2-carboxylic acid in 50 ml of tetrahydrofuran was treated with 1.5 g of 1,1'-carbonyldiimidazole and allowed to stand at room temperature for 4 hours. A solution of 1.15 g of 1H-imidazole-1-ethanamine in 25 ml of tetrahydrofuran was added and the reaction mixture was heated at reflux temperature for 3 hours, treated with 10 ml of water and again heated for one hour and then concentrated to remove the solvent. The residue was shaken with 5 ml of 1N sodium hydroxide and 300 ml of dichloromethane and the layers were separated. The organic layer was washed with water, dried over magnesium sulfate and concentrated to recover the desired compound, mp 167°–169° C.

EXAMPLE 33

N-[3-(2-Phenyl-1H-imidazol-1-yl)propyl]-1H-indole-2-carboxamide

A mixture of 2.42 g of indole-2-carboxylic acid and 2.43 g of 1,1'-carbonyldiimidazole in 60 ml of tetrahydrofuran was stirred at room temperature for 2 hours. Then 3.0 g of 2-phenyl-1H-imidazole-1-propanamine was added and the mixture was stirred at room temperature for 16 hours. The mixture was heated at reflux for 2 hours then 10 ml of water was added and heating was continued for one hour longer. The mixture was concentrated and 50 ml of dichloromethane and 10 ml of 1N sodium hydroxide were added with shaking. The organic layer was separated, washed twice with water and dried over magnesium sulfate, then concentrated in vacuo and gave 5.9 g of a viscous oil. The oil was treated by preparative high pressure liquid chromatography using a PrepPAK ®-500 silica column (Waters Associates, Millipore) and ethyl acetate as eluent. Fractions were collected and fractions 5 and 6 were concentrated and gave 3.0 g of a glass. The glass was treated with ether and a cream colored precipitate gradually formed and was collected by filtration to give 2.4 g of the desired compound as a cream colored solid, mp 167°–169° C.

EXAMPLE 34

N-[3-(4-Phenyl-1H-imidazol-1-yl)propyl]-1H-indole-2-carboxamide

The compound of this Example is obtained when indole-2-carboxylic acid is reacted with 1,1'-carbonyldiimidazole and 4-phenyl-1H-imidazole-1-propanamine by the procedure of Example 33.

EXAMPLE 35

5-Chloro-N-[3-(1H-imidazol-1-yl)-2-methylpropyl]-1Hindole-2carboxamide

The compound of this Example, mp 200°-203° C., was obtained when 5-chloroindole-2-carboxylic acid was reacted with 1,1'-carbonyldiimidazole and 3-(1H-imidazole)-2-methyl-1-propanamine by the procedure of Example 33.

EXAMPLE 36

5-Chloro-N-[3-(1H-imidazol-1-yl)-butyl]-1H-indole-2-carboxamide

When 5-chloroindole-2-carboxylic acid was reacted with 1,1'-carbonyldiimidazole and 3-(1H-imidazole)-1-butanamine by the procedure of Example 33, the compound of this Example, mp 210° C., was obtained.

We claim:

1. A compound of the formula:

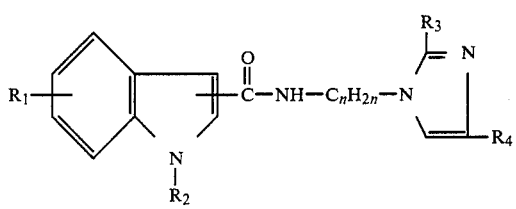

wherein $R_1$ is selected from the group consisting of hydrogen, halogen, alkyl($C_1$–$C_3$) and alkoxy ($C_1$–$C_3$); $R_2$ is selected from the group consisting of hydrogen, alkyl ($C_1$–$C_3$) and benzyl; n is an integer from 2 to 8 inclusive; $R_3$ and $R_4$ are each individually selected from the group consisting of hydrogen, alkyl ($C_1$–$C_3$) and phenyl; or a pharmaceutically acceptable acid-addition salt thereof.

2. The compound according to claim 1; N-[3-(1H-imidazol-1-yl)propyl]-1-methyl-1H-indole-2-carboxamide.

3. The compound according to claim 1; N-[3-(1H-imidazol-1-yl)propyl]-5-methoxy-1H-indole-2-carboxamide.

4. The compound according to claim 1: N-[-3-1H-imidazol-1-yl)propyl]-1H-indole-2-carboxamide.

5. The compound according to claim 1; N-[-3-(1H-imidazol-1-yl)propyl]-1H-indole-5-carboximide.

6. The compound according to claim 1; 5-chloro-N-[3-(1Himidazol-1-yl)propyl]-1H-indole-2-carboxamide.

7. The compound according to claim 1; 1-methyl-N-[3-(4-methyl-1H-imidazol-1-yl)proply]-1H-indole-2-carboxamide.

8. The compound according to claim 1; 5-chloro-N-[3-(4-methyl-1H-imidazol-1-yl)propyl]-1H-indole-2-carboxamide.

9. The compound according to claim 1; N-[4-(1H-imidazol-1-yl)butyl]-1H-indole-2-carboxamide.

10. The compound according to claim 1; 5-methoxy-N-[4-(1H-imidazol-1-yl)butyl]-1H-indole-2-carboxamide.

11. The compound according to claim 1; N-[3(2-methyl-1H-imidazol-1-yl)propyl]-1H-indole-2-carboximide.

12. The compound according to claim 1; 5-methoxy-N-[3-(2-methyl-1H-imidazol-1-yl)propyl]-1H- indole-2-carboxamide.

13. The compound according to claim 1; N-[3-(2-methyl-1H-imidazol-1-yl)propyl]-1H-indole-5-carboxamide.

14. The compound according to claim 1; N-[3-(2-phenyl-1H-imidazol-1-yl)propyl]-1H-indole-2-carboxamide.

15. The compound according to claim 1; 1-methyl-N-[3-(2-methyl-1H-imidazol-1-yl)propyl]-1H-indole-2-carboxamide.

16. The compound according to claim 1; 5-chloro-N-[5-(1H-imidazol-1-yl)pentyl]-1H-indole-2-carboxamide.

17. The compound according to claim 1; 5-chloro-N-[4-(1H-imidazol-1-yl)butyl]-1H-indole-2-carboxamide.

18. The compound according to claim 1; 5-chloro-N-[8-(1H-imidazol-1-yl)octyl]-1H-indole-2-carboxamide.

19. The compound according to claim 1; N-[3-(4-methyl-1H-imidazol-1-yl)-propyl]-1H-indole-2-carboxamide.

20. The compound according to claim 1; N-[3-(1H-imidazol-1-yl)-propyl]-5-methyl-1H-indole-2-carboxamide.

21. The compound according to claim 1; 5-fluoro-N-[3-(1H-imidazol-1-yl)propyl]-1H-indole-2-carboxamide.

22. The compound according to claim 1; N-[3-(2-ethyl-1H-imidazol-1-yl)propyl]-1-methyl-1H-indole-2-carboxamide.

23. The compound according to claim 1; 1-benzyl-N-[4-(1H-imidazol-1-yl)butyl]-1H-indole-2-carboxamide.

24. The compound according to claim 1; 5-chloro-N-[6-(1H-imidazol-1-yl)hexyl]-1H-indole-2-carboxamide.

25. The compound according to claim 1; 5-bromo-1-methyl-N-[3-(2-methyl-1H-imidazol-1-yl)propyl]-1H-indole-2-carboxamide.

26. The compound according to claim 1; 5-chloro-N-[2-(1H-imidazol-1-yl)ethyl]-1H-indole-2-carboxamide.

27. The compound according to claim 1; N-[3-(2-phenyl-1H-imidazol-1-yl)propyl]-1H-indole-2-carboxamide.

28. The compound according to claim 1; N-[3-(4-phenyl-1H-imidazol-1-yl)propyl]-1H-indole-2-carboxamide.

29. The compound according to claim 1; 5-chloro-N-[3-(1H-imidazol-1-yl)-2-methylpropyl]-1H-indole-2-carboxamide.

30. The compound according to claim 1; 5-chloro-N-[3-(1H-imidazol-1-yl)-butyl]-1H-indole-2-carboxamide.

31. A method of inhibiting thromboxane synthetase enzyme in a mammal which comprises administering internally to said mammal an effective amount of a compound of the formula as recited in claim 1.

32. A method of lowering elevated blood pressure in a mammal which comprises administering internally to said mammal an effective amount of a compound of the formula as recited in claim 1.

33. A thromboxane synthetase enzyme inhibiting composition of matter in dosage unit form which comprises an effective amount of a compound of the formula as recited in claim 1 in association with a pharmaceutically acceptable carrier.

34. A thromboxane synthetase enzyme inhibiting composition of matter, as recited in claim 33, wherein the dosage unit comprises from about 10 mg to about 700 mg of the compound in association with the pharmaceutically acceptable carrier.

35. A therapeutic composition of matter in dosage unit form useful for lowering elevated blood pressure in mammals which comprises an effective amount of a compound of the formula as recited in claim 1 in association with a pharmaceutically acceptable carrier.

36. A therapeutic composition of matter as recited in claim 35 wherein the dosage unit comprises from about 10 mg to 700 mg of the compound in association with the pharmaceutically acceptable carrier.

* * * * *